(12) United States Patent
Goossens et al.

(10) Patent No.: US 10,378,036 B2
(45) Date of Patent: Aug. 13, 2019

(54) METHOD FOR THE REGIOSELECTIVE DEACETYLATION OF MANNOSYLERYTHRITOL LIPIDS

(71) Applicant: Universiteit Antwerpen, Antwerp (BE)

(72) Inventors: Eliane Yvonne Goossens, Niel (BE); Marc Victor Henri Wijnants, Tielt-Winge (BE)

(73) Assignee: Universiteit Antwerpen, Antwerp (BE)

( * ) Notice: Subject to any disclaimer, the term of this patent is extended or adjusted under 35 U.S.C. 154(b) by 51 days.

(21) Appl. No.: 15/552,860

(22) PCT Filed: Mar. 1, 2016

(86) PCT No.: PCT/EP2016/054284
§ 371 (c)(1),
(2) Date: Aug. 23, 2017

(87) PCT Pub. No.: WO2016/139190
PCT Pub. Date: Sep. 9, 2016

(65) Prior Publication Data
US 2018/0037916 A1    Feb. 8, 2018

(30) Foreign Application Priority Data

Mar. 2, 2015 (EP) .................................... 15157218

(51) Int. Cl.
*C12P 19/44* (2006.01)
*C12P 7/64* (2006.01)

(52) U.S. Cl.
CPC ............. *C12P 19/44* (2013.01); *C12P 7/6436* (2013.01); *C12Y 301/01003* (2013.01)

(58) Field of Classification Search
None
See application file for complete search history.

(56) References Cited

PUBLICATIONS

Doukyu et al. Biochem. Engineering Journal (2010) 48: 270-282 (Year: 2010).*
Sabaini et al. J. Molec. Catal. B: Enzymatic (2010) 62: 225-229 (Year: 2010).*
Secundo et al. Chem. Eur. J. (2003) 9: 3194-3199 (Year: 2003).*
Cabrera et al. J. Molec. Catal. B: Enzymatic (2009) 57: 171-176 (Year: 2009).*
"Enzymatic synthesis of a novel glycolipid biosurfactant, mannosylerythritol lipid-D and its aqueous phase behavior", Fukuoka, T., et al., Carbohydrate Research, 346 (2011), 266-271.
"Investigation of the causes of deactivation-degradation of the commercial biocatalyst Novozym (R) 435 in ethanol and ethanol-acqueous media", Jose, C., et al., Journal of Molecular Catalyst B: Enzymatic, 71 (2011), 95-107.
"Fed-batch bioreactor production of mannosylerythritol lipids secreted by Pseudozyma aphidis", Rau, et al., Biotechnological Products and Process Engineering, 2005, vol. 68, pp. 607-613.
"Lipase-mediated deacetylation and oligomerization of lactonic sophorolipids", Hu Yongmei, et al., Biotechnology Progress, American Institute of Chemical Engineers, US, vol. 19, Mar. 1, 2003, pp. 303-311.
"Lipase-catalyzed asymmetric acylation in the chemoenzymatic synthesis of furan-based alcohols", Nara et al., Tetrahedron Asymmetry, Pergamon Press, Ltd., Oxford, GB, vol. 24, Feb. 12, 2013 pp. 142-150.
International Search Report and Written Opinion dated May 23, 2016 for PCT/EP2016/054284 Filed Mar. 1, 2016. pp. 1-11.
European Search Report dated Aug. 18, 2015 for Application No. 15157218.7 filed Mar. 2, 2015. pp. 1-7.
"Formation and analysis of mannosylerythritol lipids secreted by Pseudozyma aphidis", Rau, et al., Applied Microbial and Cell Physiology, 2005, vol. 66, pp. 551-559.

* cited by examiner

*Primary Examiner* — Susan M Hanley
(74) *Attorney, Agent, or Firm* — Dinsmore & Shohl, LLP

(57) ABSTRACT

The present invention relates to methods for the enzymatic deacetylation of mannosylerythritol lipids produced by fermentation using lipases. More in particular, the present invention relates to a method for the enzymatic deacetylation of mannosylerythritol lipids using a hydrolyzing enzyme in an organic solvent containing only low amounts of water, preferably, no water. It further provides the use of organic solvents, containing only low amounts of water, more preferably, no water, for the enzymatic deacetylation of mannosylerythritol lipids.

12 Claims, 7 Drawing Sheets

METHOD FOR THE REGIOSELECTIVE DEACETYLATION OF MANNOSYLERYTHRITOL LIPIDS

FIELD OF THE INVENTION

The present invention relates to methods for the enzymatic deacetylation of mannosylerythritol lipids produced by fermentation. More in particular, the present invention relates to a method for the enzymatic deacetylation of mannosylerythritol lipids using a lipase in an organic solvent containing only low amounts of water, preferably, no water. It further provides the use of organic solvents, containing only low amounts of water, more preferably, no water, for the enzymatic deacetylation of mannosylerythritol lipids.

BACKGROUND TO THE INVENTION

Upon cultivation with vegetable oils such as soybean oil or rapeseed oil, Pseudozyma aphidis produces extracellular biosurfactants, named mannosylerythritol lipids (MELs) (Rau et al., 2005). These are considered very promising due to their high fermentation yields (over 100 g/l) and excellent surface-active and potential pharmaceutical properties. The fermentation product consists of a complex mix of residual free fatty acids and four types of MELs with different degrees of acetylation. These four MEL types are classified as MEL-A, -B, -C and -D, and are hereinafter referred to as formulae (Ia), (Ib), (Ic) and (Id) respectively.

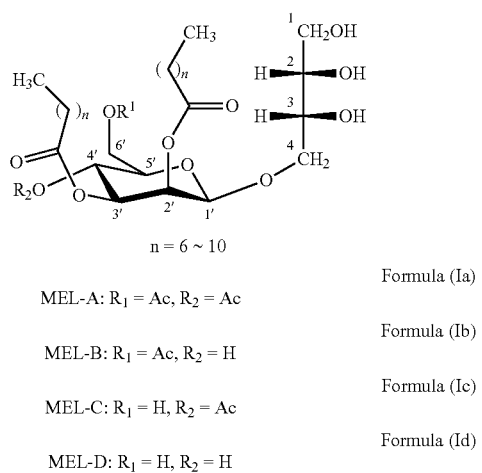

MEL-A: $R_1$ = Ac, $R_2$ = Ac  Formula (Ia)

MEL-B: $R_1$ = Ac, $R_2$ = H  Formula (Ib)

MEL-C: $R_1$ = H, $R_2$ = Ac  Formula (Ic)

MEL-D: $R_1$ = H, $R_2$ = H  Formula (Id)

Said MEL types have respectively two acetyl (Ac) groups on C4' and C6', one acetyl group on C6', one acetyl group on C4' and no acetyl groups at all on the mannose moiety. MEL-A with the highest acetylation degree represents 50-60% of the total MELs, MEL-B 12-17%, MEL-C 20-33% and MEL-D only 5-10%.

Acetylated products are known to be hydrolytically unstable, resulting in the unwanted release of acetic acid with a penetrating odor as a consequence and hereby compromising product quality and stability, especially for applications such as in food or cosmetics. An additional advantage of the deacetylated MELs is the reduced complexity of the fermentation product, which simplifies its purification.

Chemical hydrolysis of (acetyl)esters is widely applied, resulting in a carboxylic acid (acetic acid) and an alcohol. To catalyze these reactions a high pH is required. Usually a base such as KOH or NaOH is used. However, alkaline hydrolysis is an aggressive method and would in this case hydrolyze all ester bonds present in the MEL molecule, thereby removing its fatty acyl chains which form the hydrophobic tail of the surfactant.

To address this issue, enzymatic deacetylation can be used as a mild alternative. Under carefully selected process conditions, enzymes can catalyze specific reactions. Fukuoka et al. (2011) reported the enzymatic deacetylation of mannosylerythritol lipids using a lipase and a water-containing organic solvent. In particular, Fukuoka discloses the enzymatic deacetylation of a diastereomer of MEL-B produced by the yeast Pseudozyma tsukubaensis using the lipase from Candida antarctica immobilized on acrylic resin, i.e. Novozym® 435. The solvent used was 90% ethanol (thus containing 10% water). The reaction took 7 days resulting in a conversion of >99% starting from 50 g/l MEL-B. The calculated productivity (grams of substrate conversion per liter per day) of this reaction, based on Fukuoka's results, is approximately 7 g/l·d using 25 g/l of Novozym® 435 with an activity of 10,000 PLU/g. Such long reaction times, i.e. seven days or more, are typical for enzymatic deacetylation reactions of glycolipid biosurfactants (Fukuoka et al., 2011; Hu et al., 2003). For the conventional MEL-A (as opposed to the diastereomer), Fukuoka et al., 2011 only partially obtained a MEL which was more hydrophilic, namely MEL-C instead of MEL-D. As detailed in the examples that follow herein after, a repetition of the experiments by Fukuoka et al., using 90% ethanol (+10% water) was performed. However, this resulted in a very low and slow conversion (only 18 conversion after 24 h-72 h). On the other hand, a parallel experiment in accordance with the current invention was carried out where water was omitted from the reaction solvent. Absolute ethanol was used here resulting in a vast improvement of the deacetylation of the conventional MEL-B (91% conversion after 24 h).

These data further support that for enzymatic reactions, the reaction conditions and solvents are crucial, and preferably do not cause the denaturation of the enzymes, since these are in general very expensive and thus preferably reused after the reaction. Polar solvents like water, and methanol are known to have a detrimental effect on free lipases and immobilized lipases such as Novozym® 435, especially at their optimal working temperatures >45° C. (José et al., 2011)

It was thus an object of the present invention to provide a more suitable reaction medium for the deacetylation of mannosylerythritol lipids, wherein the enzyme doesn't suffer major activity loss and can be reused. Furthermore, it was an object of the present invention to reduce the reaction time, to make the process economically feasible.

SUMMARY OF THE INVENTION

In a first aspect, the present invention provides a method for the enzymatic deacetylation of a mannosylerythritol lipid represented by formula (I)

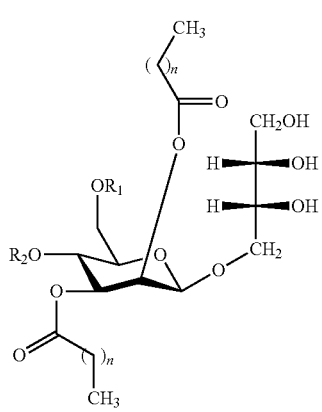

(I)

wherein
  $R_1$ and $R_2$ are each independently selected from —H and —Ac;
  at least one of $R_1$ and $R_2$ is —Ac; and
  n=6-10
said method comprising: incubating a mannosylerythritol lipid represented by formula (I), with a hydrolyzing enzyme in an organic solvent containing less than 10% water; in particular said organic solvent is selected from the list comprising C2-C8 alcohols, and combinations thereof.

In a particular embodiment, the present invention provides a method for the enzymatic deacetylation of a mannosylerythritol lipid represented by formula (Ia), to obtain a mannosylerythritol lipid represented by formula (Ic),

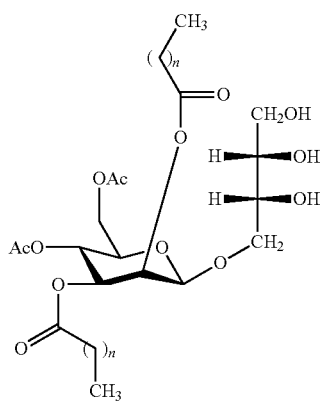

(Ia)

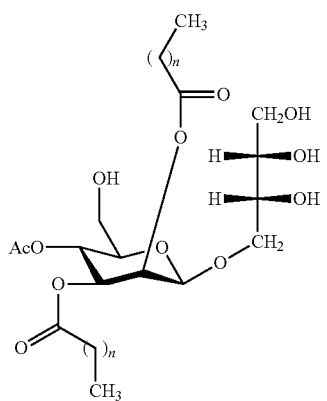

(Ic)

said method comprising: incubating a mannosylerythritol lipid represented by formula (Ia), with a hydrolyzing enzyme in an organic solvent containing less than 10% water; in particular said organic solvent is selected from the list comprising C2-C8 alcohols, and combinations thereof.

In yet a further embodiment, the present invention provides a method for the enzymatic deacetylation of a mannosylerythritol lipid represented by formula (Ib), to obtain a mannosylerythritol lipid represented by formula (Id),

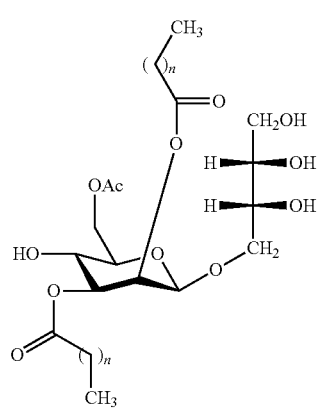

(Ib)

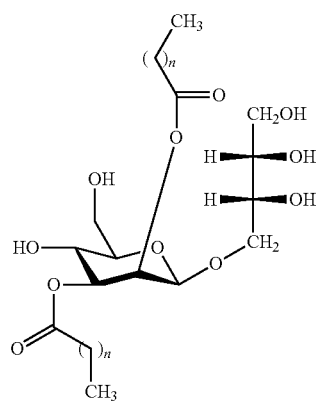

(Id)

said method comprising: incubating a mannosylerythritol lipid represented by formula (Ib), with a hydrolyzing enzyme in an organic solvent containing less than 10% water; in particular said organic solvent is selected from the list comprising C2-C8 alcohols, and combinations thereof.

In another particular embodiment, the present invention provides a method for the enzymatic deacetylation of a mannosylerythritol lipid represented by formula (Ia), to obtain a mannosylerythritol lipid represented by formula (Id), (Ia)

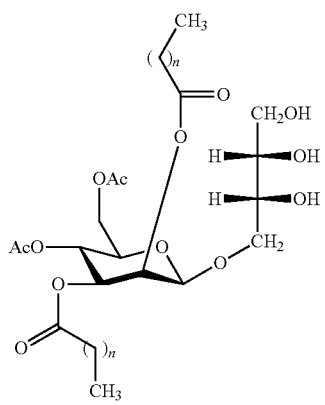

(Id)

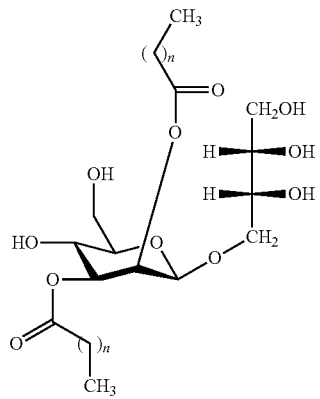

(Id)

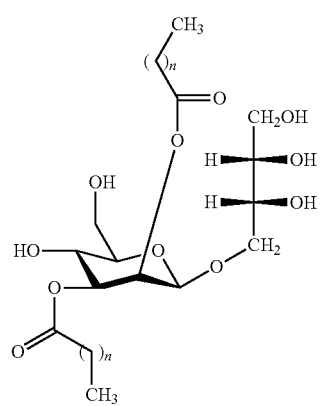

said method comprising: incubating a mannosylerythritol lipid represented by formula (Ia), with a hydrolyzing enzyme in an organic solvent containing less than 10% water; in particular said organic solvent is selected from the list comprising C2-C8 alcohols, and combinations thereof.

In yet another particular embodiment, the present invention provides a method for the enzymatic deacetylation of a mannosylerythritol lipid represented by formula (Ic), to obtain a mannosylerythritol lipid represented by formula (Id), (Ic)

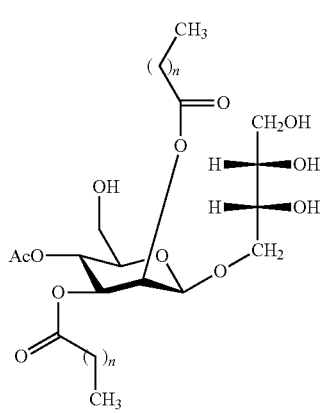

said method comprising: incubating a mannosylerythritol lipid represented by formula (Ia), with a hydrolyzing enzyme in an organic solvent containing less than 10% water; in particular said organic solvent is selected from the list comprising C2-C8 alcohols, and combinations thereof.

In a further aspect, the present invention provides the use of an organic solvent, in the enzymatic deacetylation of a mannosylerythritol lipid represented by formula (I)

(I)

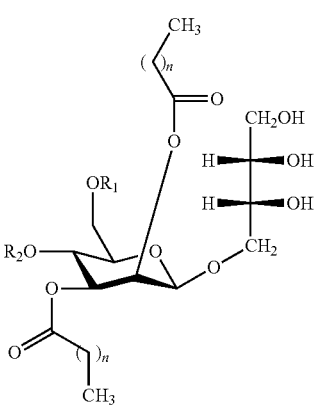

wherein
R$_1$ and R$_2$ are each independently selected from —H and —Ac;
at least one of R$_1$ and R$_2$ is —Ac; and
n=6-10
wherein said organic solvent is selected from the list comprising C2-C8 alcohols, and combinations thereof; and wherein said organic solvent contains less than 10% water.

In a particular embodiment of the present invention, said organic solvent preferably contains less than 9%, 8%, 7%, 6%, 5%, 4%, 3%, 2%, or 1% water, most preferably, said organic solvent contains no additional water.

In a particular embodiment, of the present invention, said hydrolyzing enzyme is a lipase. More in particular, said lipase is a *Candida antarctica* lipase B.

In yet a further embodiment of the present invention, said organic solvent is selected from the list comprising THF, toluene, cyclohexane, short-chain alcohols (1-3 C atoms) or long-chain alcohols (4-10 C atoms). More in particular, said organic solvent is selected from the list comprising linear and branched C2-C8 alcohols; in particular ethanol, 1-propanol, 1-butanol, 1-pentanol, 1-hexanol, 1-heptanol, 1-octanol, isopropanol, isobutanol, t-butanol, 2-pentanol, isoamyl alcohol, 2-ethylhexanol, cyclohexanol . . . .

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
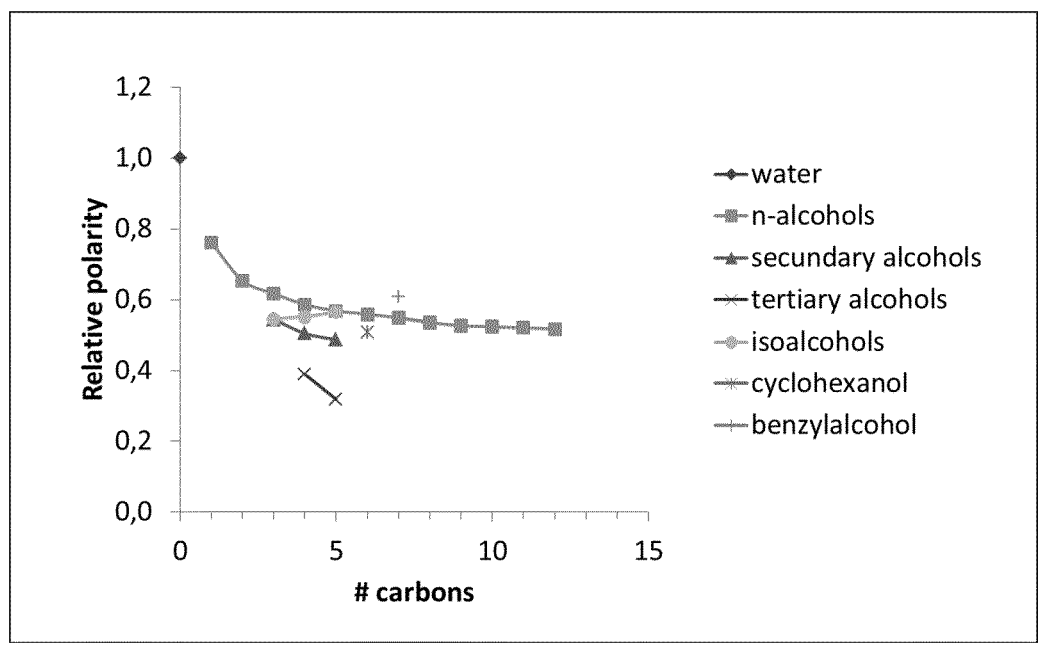
FIG. 1: Relative solvent polarities extracted from Table A-1 (Reichardt, 2003))

As already indicated herein before, the present invention provides a method for the enzymatic deacetylation of a mannosylerythritol lipid represented by formula (I)

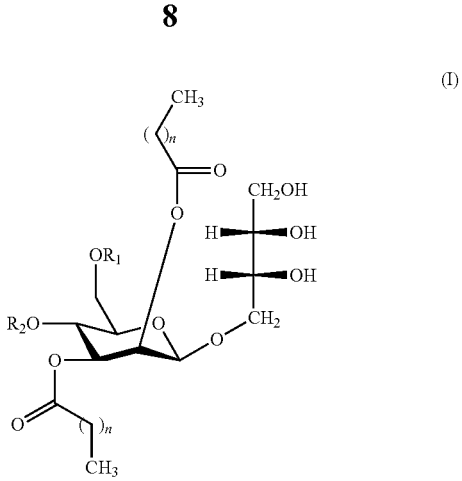

wherein
$R_1$ and $R_2$ are each independently selected from —H and —Ac;
at least one of $R_1$ and $R_2$ is —Ac; and
n=6-10
said method comprising: incubating a mannosylerythritol lipid represented by formula (I), with a hydrolyzing enzyme in an organic solvent containing less than 10% water; in particular said organic solvent is selected from the list comprising C2-C8 alcohols, and combinations thereof.

Hence, the present invention comprises a process for regiospecific deacetylation of MEL-A and -B to form MEL-C and -D, by using an enzyme that hydrolyses ester bonds. The hydrolyzing enzyme is preferably a lipase, more preferably Novozym® 435 and the reaction occurs in an organic solvent such as THF, toluene or cyclohexane, or alcohols such as ethanol, propanol, butanol, pentanol, hexanol, heptanol and octanol, in which all MEL-types dissolve; however in low amounts or water (i.e. less than 10%), preferably in the absence of water.

Typically, following Rau et al.'s publication (Rau et al., 2005), for the fermentative synthesis of MELs, *Pseudozyma aphidis* is first grown on a seed culture medium containing in one liter, 30 g glucose, 1 g $NH_4NO_3$, 0.3 g $KH_2PO_4$, 1 g yeast extract, pH 6.0 not adjusted, incubation time 2 days. The main culture medium contains in one liter, 80 ml vegetable oil (either soybean oil or rapeseed oil), 2 g $NaNO_3$, 0.2 g $KH_2PO_4$, 0.2 g $MgSO_4 \cdot 7H_2O$, 1 g yeast extract, pH 6.2 not adjusted. The seed culture is inoculated from agar slants and incubated at 30° C. and shaken or stirred at a speed depending on the volume of the flask or reactor. The main culture is inoculated with 10% of its volume with the seed culture and incubated at 27° C. The culture suspension is extracted with either ethyl acetate or MTBE followed by paper filtration of the organic phase. The organic phase is then evaporated by rotary vacuum concentration. The remaining sticky phase is washed with 600 ml n-hexane-methanol-water (1:6:3) to remove the remaining oil and fatty acids (top phase). The aqueous phase (bottom phase) is washed twice with 100 ml n-hexane. After removal of methanol and water by vacuum evaporation, the remaining product contains a mix of MEL-A, -B, -C and -D. This mix is used as reference for TLC analyses.

To further purify MEL-A, -B, -C and -D, this MEL-mix is separated by column chromatography using silica gel as the stationary phase and different proportions of chloroform and acetone for elution, as described previously by Kitamoto et al., 1990.

In this research, 12 enzymes were tested for their ability to selectively deacetylate MELs without affecting the other ester bonds in the glycolipid structure. Using *Candida antarctica* lipase B (Novozym® 435), the regioselective deacetylation of conventional MELs was successful and resulted in two MEL types: MEL-C and MEL-D

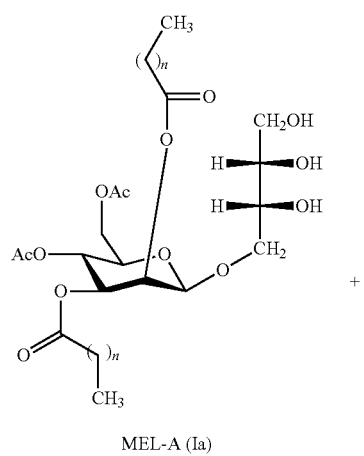

MEL-A (Ia)

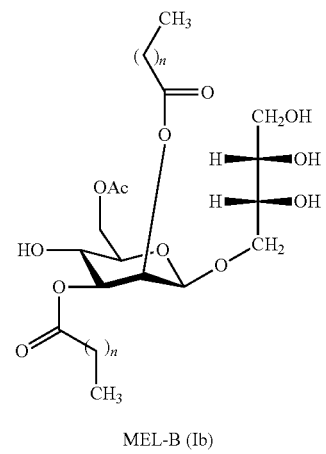

MEL-B (Ib)

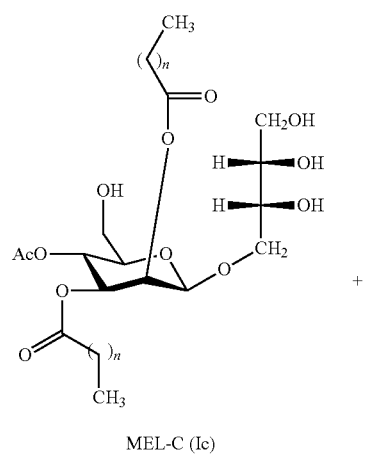

MEL-C (Ic)

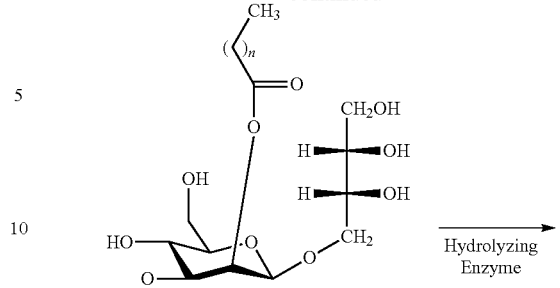

MEL-D (Id)

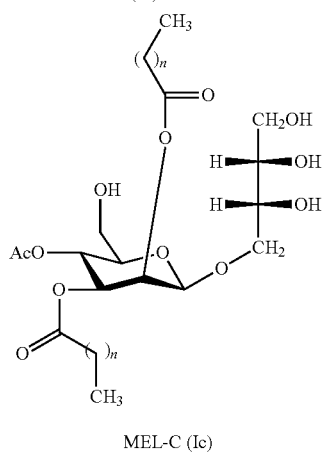

MEL-C (Ic)

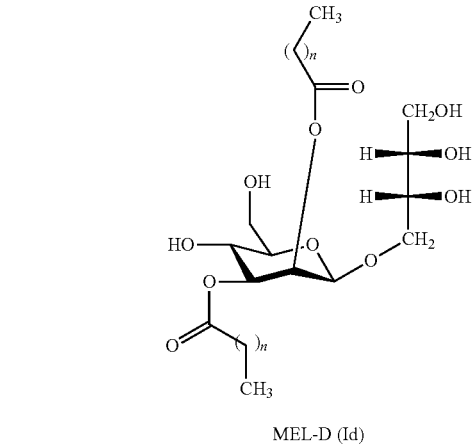

MEL-D (Id)

The successful reaction with *Candida antarctica* lipase B (Novozym® 435) was further optimized by screening solvents with different polarities, resulting in a 100% conversion and a shorter reaction time. In particular, solvents being alcohols with a carbon chain length of C2 to C8 appeared to be suitable; more in particular long-chain alcohols, i.e. n-alcohols with a carbon chain length of C5 to C8, proved to be the most suitable; and the reaction time could be reduced to hours instead of days as for the process of Fukuoka et al., 2011.

When looking at the relative polarities of different alcohols (FIG. 1), It was further found that the more apolar the solvent, the better the results were and that this was also related to the polarity of the MEL, more in particular, MEL-A is less polar than MEL-B, so for its deacetylation a less polar alcohol is needed to reach the same reaction rate as with MEL-B. This trend is probably a consequence of the substrate's solubility: the better soluble the higher the reaction rate.

In the context of the present invention, the term "solvent" is to be understood as being a substance that dissolves a mannosylerythritol lipid, thereby resulting in a solution. A mix of another organic solvent which dissolves MELs in combination with an alcohol can be used as well as long as there is enough alcohol present to participate in the reaction.

In a particular embodiment of the present invention, said organic solvent is selected from the list comprising THF, toluene, cyclohexane, short-chain alcohols (1-3 C atoms) or long-chain alcohols (4-10 C atoms). More in particular, said organic solvent is selected from the list comprising linear and branched C2-C8 alcohols; in particular ethanol, propanol, isopropanol, 1-butanol, 2-pentanol, iso amylalcohol, t-butanol, pentanol, heptanol, octanol.

In the context of the present invention, the term "alcohol", is meant to include monohydric alcohols (i.e. having one functional —OH group), as well as polyhydric alcohols (i.e. having 2 or more functional —OH groups). Examples of monohydric alcohols include ethanol, propanol, isopropanol, 1-butanol, 2-pentanol, isoamyl alcohol, t-butanol, pentanol, heptanol, octanol. Examples of polyhydric alcohols, such as bihydric alcohols include glycols such as ethylene glycol, propylene glycol and butylene glycol. In a particular embodiment, the alcohols of the present invention are monohydric alcohols. In another particular embodiment, the alcohols of the present invention are polyhydric alcohols.

Especially, the used solvents, i.e. alcohol+water (less than 10%) have a polarity less than that of ethanol. Hence, the reaction is performed in as little water as possible (preferably in the absence of water) in particular for those alcohols, which are rather polar, such as ethanol.

In a particular embodiment of the present invention, said organic solvent preferably contains less than 9%, 8%, 7%, 6%, 5%, 4%, 3%, 2%, or 1% water, most preferably, said organic solvent contains no additional water.

In the context of the present invention, the hydrolysing enzyme is preferably a lipase; even more preferably a *Candida antarctica* lipase B preferably immobilized for easier recovery and reuse. More in particular, the lipase is selected from the list comprising; Nozozym® 435, CalB immo Plus, CalB immo 8285, CalB immo 8806, CalB immo 1090, CalB immo 5587, CalB immo 5872, . . . ; preferably Novozym® 435. Lipases are generally classified using the following enzyme classification No EC 3.1.1.3.

The process of the present invention was shown to be suitable for the conversion of: MEL-A to MEL-C, MEL-B to MEL-D, MEL-C to MEL-D and MEL-A to MEL-D. The conversion of MEL-A to MEL-D is regioselective and occurs in a 2-step process i.e. the initial conversion of MEL-A to MEL-C, followed by the conversion of MEL-C to MEL-D.

Hence, in a particular embodiment, the present invention provides a method for the enzymatic deacetylation of a mannosylerythritol lipid represented by formula (Ia), to obtain a mannosylerythritol lipid represented by formula (Ic),

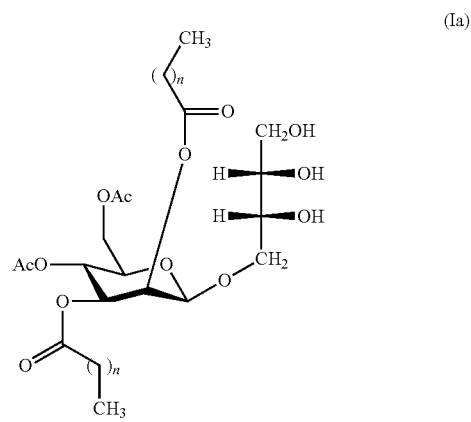

(Ia)

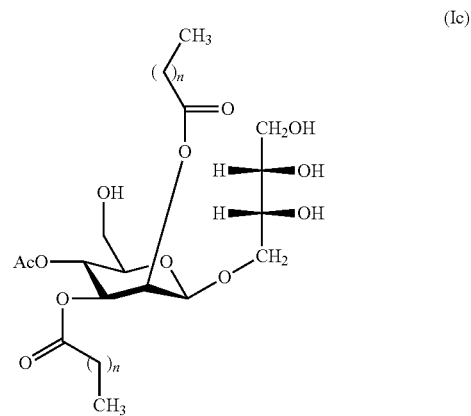

(Ic)

said method comprising: incubating a mannosylerythritol lipid represented by formula (Ia), with a hydrolyzing enzyme in an organic solvent containing less than 10% water; in particular said organic solvent is selected from the list comprising C2-C8 alcohols, and combinations thereof.

In yet a further embodiment, the present invention provides a method for the enzymatic deacetylation of a mannosylerythritol lipid represented by formula (Ib), to obtain a mannosylerythritol lipid represented by formula (Id),

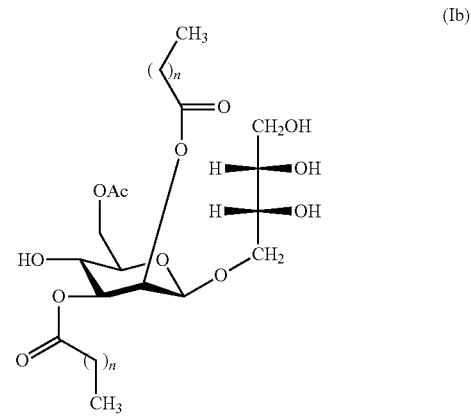

(Ib)

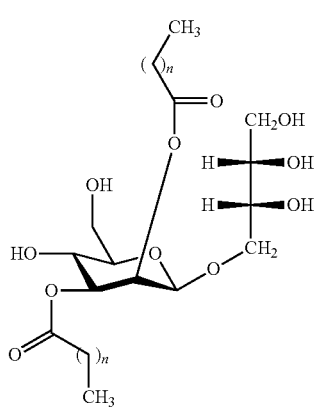

(Id)

said method comprising: incubating a mannosylerythritol lipid represented by formula (Ib), with a hydrolyzing enzyme in an organic solvent containing less than 10% water; in particular said organic solvent is selected from the list comprising C2-C8 alcohols, and combinations thereof.

In another particular embodiment, the present invention provides a method for the enzymatic deacetylation of a mannosylerythritol lipid represented by formula (Ia), to obtain a mannosylerythritol lipid represented by formula (Id),

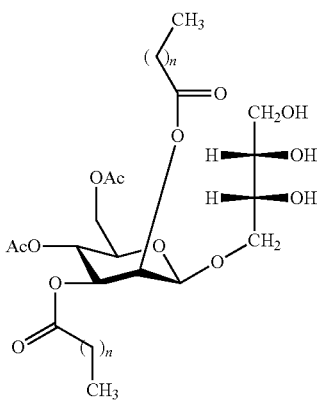

(Ia)

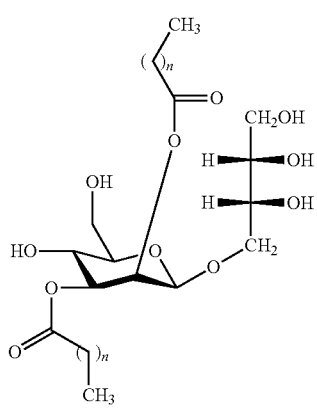

(Id)

said method comprising: incubating a mannosylerythritol lipid represented by formula (Ia), with a hydrolyzing enzyme in an organic solvent containing less than 10% water; in particular said organic solvent is selected from the list comprising C2-C8 alcohols, and combinations thereof.

In yet another particular embodiment, the present invention provides a method for the enzymatic deacetylation of a mannosylerythritol lipid represented by formula (Ic), to obtain a mannosylerythritol lipid represented by formula (Id),

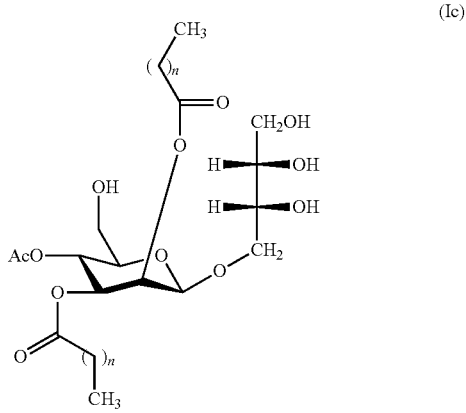

(Ic)

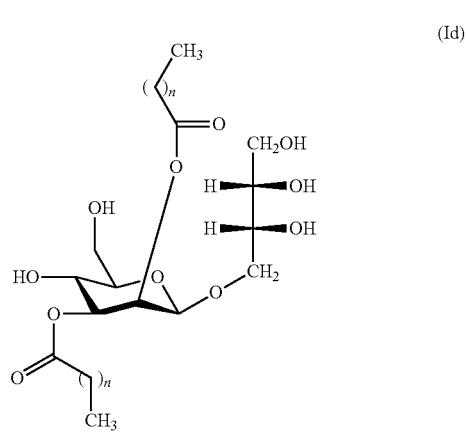

(Id)

said method comprising: incubating a mannosylerythritol lipid represented by formula (Ia), with a hydrolyzing enzyme in an organic solvent containing less than 10% water; in particular said organic solvent is selected from the list comprising C2-C8 alcohols, and combinations thereof.

As evident from the examples that follow herein after, and as discussed herein before, the inventors have found that the use of the claimed organic solvents, in limited amounts of water, is highly beneficial in an enzymatic deacetylation reaction of mannosylerythritol lipids.

Therefore, in a further aspect, the present invention provides the use of an organic solvent, in the enzymatic deacetylation of a mannosylerythritol lipid represented by formula (I)

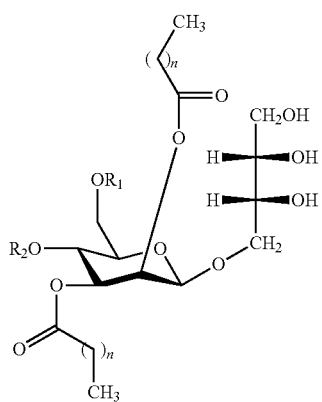

(I)

wherein
R$_1$ and R$_2$ are each independently selected from —H and —Ac;
at least one of R$_1$ and R$_2$ is —Ac; and
n=6-10 wherein said organic solvent is selected from the list comprising C2-C8 alcohols, and combinations thereof; and wherein said organic solvent contains less than 10% water.

In a particular embodiment, the present invention provides the use of an organic solvent in the enzymatic deacetylation of a mannosylerythritol lipid represented by formula (Ia), to obtain a mannosylerythritol lipid represented by formula (Ic) wherein said organic solvent is selected from the list comprising C2-C8 alcohols, and combinations thereof; and wherein said organic solvent contains less than 10% water

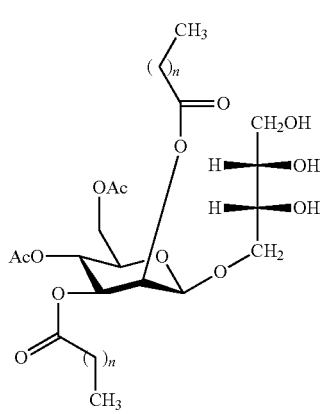

(Ia)

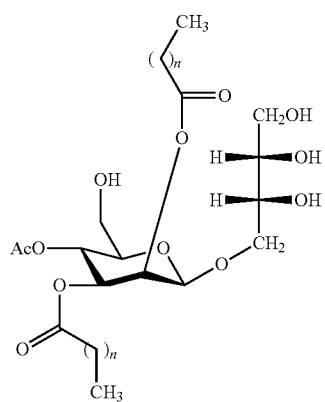

(Ic)

In a particular embodiment, the present invention provides the use of an organic solvent in the enzymatic deacetylation of a mannosylerythritol lipid represented by formula (Ib), to obtain a mannosylerythritol lipid represented by formula (Id) wherein said organic solvent is selected from the list comprising C2-C8 alcohols, and combinations thereof; and wherein said organic solvent contains less than 10% water

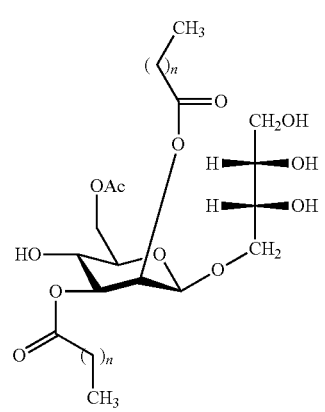

(Ib)

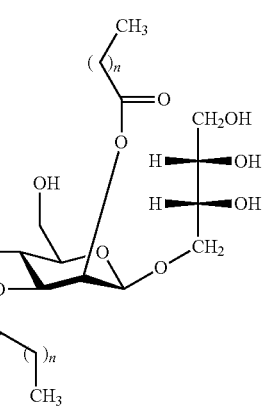

(Id)

In a particular embodiment, the present invention provides the use of an organic solvent in the enzymatic deacetylation of a mannosylerythritol lipid represented by formula (Ia), to obtain a mannosylerythritol lipid represented by formula (Id) wherein said organic solvent is selected from the list comprising C2-C8 alcohols, and combinations thereof; and wherein said organic solvent contains less than 10% water

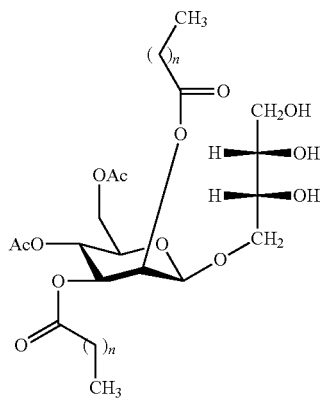

(Ia)

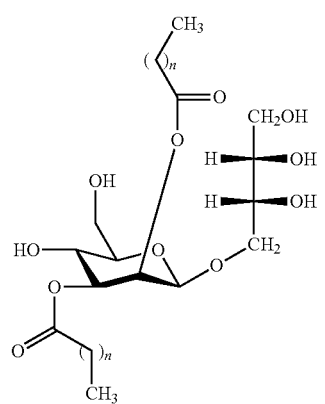

(Id)

In a particular embodiment, the present invention provides the use of an organic solvent in the enzymatic deacetylation of a mannosylerythritol lipid represented by formula (Ic), to obtain a mannosylerythritol lipid represented by formula (Id) wherein said organic solvent is selected from the list comprising C2-C8 alcohols, and combinations thereof; and wherein said organic solvent contains less than 10% water

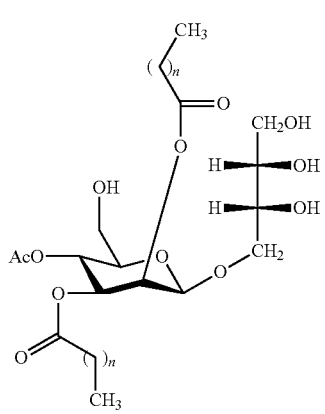

(Ic)

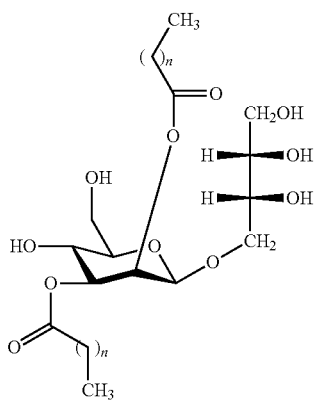

(Id)

EXAMPLES

Example 1: Omitting Water from Fukuoka et al.'s (2011) Reaction Solvent Results in a Vast Improvement of the Deacetylation Reaction of Conventional MEL-B Using Novozym® 435

Figure 2:
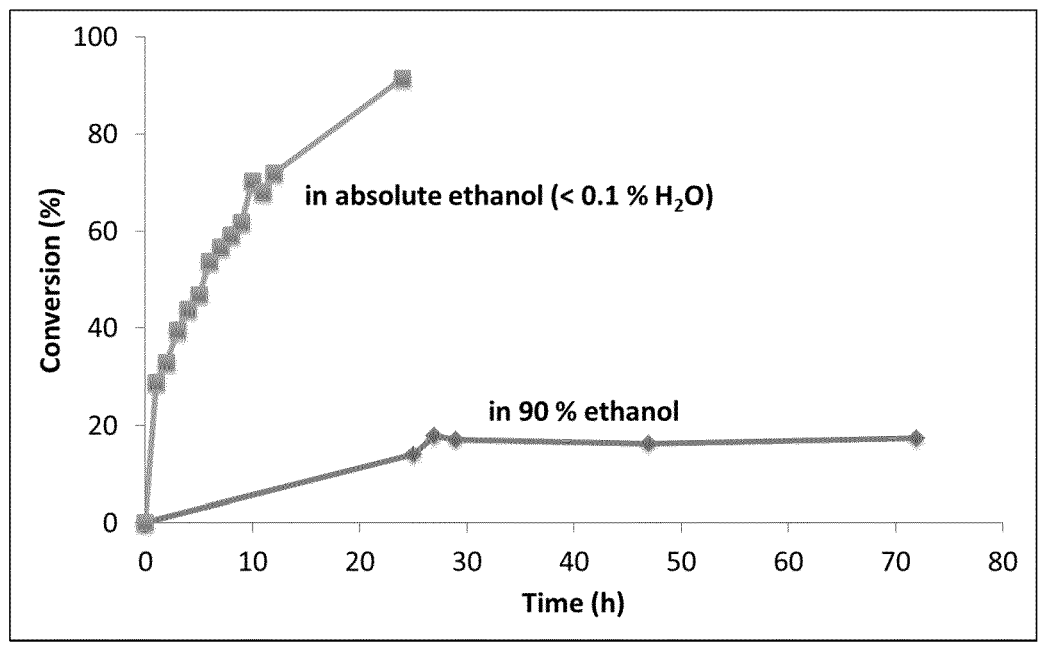
FIG. 2: Example 1—HPLC results of the enzymatic convertion of MEL-B to MEL-D in 90% ethanol and absolute ethanol.

In a first attempt for the enzymatic deacetylation of the conventional MEL-B, Fukuoka et al.'s method using 90% ethanol as the reaction solvent was replicated. (Fukuoka et al., 2011) However, this resulted in a very low and slow conversion. FIG. 1 shows an 18% conversion after 24 h and no further increase after 72 h. This means that somehow the enzyme was inactivated after 24 h, probably due to the detrimental effect of the solvent, 90% ethanol+10 water, on the enzyme and its carrier. A parallel experiment was carried out where water was omitted from the reaction solvent. Absolute ethanol was used here resulting in a vast improvement of the deacetylation of the conventional MEL-B. After 24 h the conversion reached 91%. (FIG. 2)

Materials and Methods

Two 14 g/l MEL-B solutions were prepared, one in 90% ethanol and one in absolute ethanol (<0.1% water). The deacetylation reactions were initiated by adding 50 g/l Novozym® 435 (Lipase acrylic resin from *Candida antarctica*, ≥5,000 U/g, Sigma-Aldrich, Belgium) and incubating at 60° C. and 200 rpm. Samples were taken periodically and analysed by thin layer chromatography (TLC) and high performance liquid chromatography (HPLC). Results from TLC are not shown. The reactions were terminated after 72 h.

TLC Analysis:

Qualitative results for each reaction were obtained by spotting a 1 µl of sample on a TLC (thin layer chromatography) plate (TLC plates silica gel 60, Merck) followed by elution in a TLC chamber using dichloromethane-acetone (60:40) as the solvent system. Subsequently, the compounds were located by charring at 110° C. for 5 min after spraying an orcinol (0.1% orcinol in 5% $H_2SO_4$) solution.

HPLC Analysis:

The quantitative follow-up of each reaction was carried out by HPLC (High-performance liquid chromatography) analysis using a Nova Pak® Silica Column (WATERS®, 60 Å, 4 µm, 3.9 mm×150 mm) coupled to an ELSD (Evaporating Light Scattering Detector), with a mobile phase flow-rate of 0.6 ml/min and a column temperature of 30° C. The used gradient consisted of chloroform and methanol (99:1 to 0:100) over 15 minutes. Samples were prepared by first evaporating the solvent in a vacuum centrifuge (9 mbar, 60° C.) and diluting them in chloroform to the appropriate concentration for HPLC analysis. Samples were filtered prior to analysis with 0.2 µm PTFE syringe filters to remove solids which could bring damage to the HPLC column.

Example 2: Screening of Different Organic Solvents with Different Polarities (Log P) for the Regiospecific Deacetylation of Purified MEL-A and MEL-B Materials and Methods THF, toluene, cyclohexane, ethanol, butanol, pentanol, hexanol, heptanol and octanol containing 50 g/l immobilized enzyme (Novozym® 435, ≥5000 PLU/g, Sigma-Aldrich, Belgium) and 14 g/l of conventional MEL-A (4-O-[(4',6'-di-O-acetyl-2',3'-di-O-alka-noyl)-β-D-mannopyranosyl]-meso-erythritol) or conventional MEL-B (4-O-[(6'-mono-O-acetyl-2',3'-di-O-alka-noyl)-β-D-mannopyranosyl]-meso-erythritol), were tested each for their suitability as a solvent for enzymatic deacetylation. The reaction temperature was 60° C. in each case and the shaking speed 200 rpm.

Results

Figure 3:
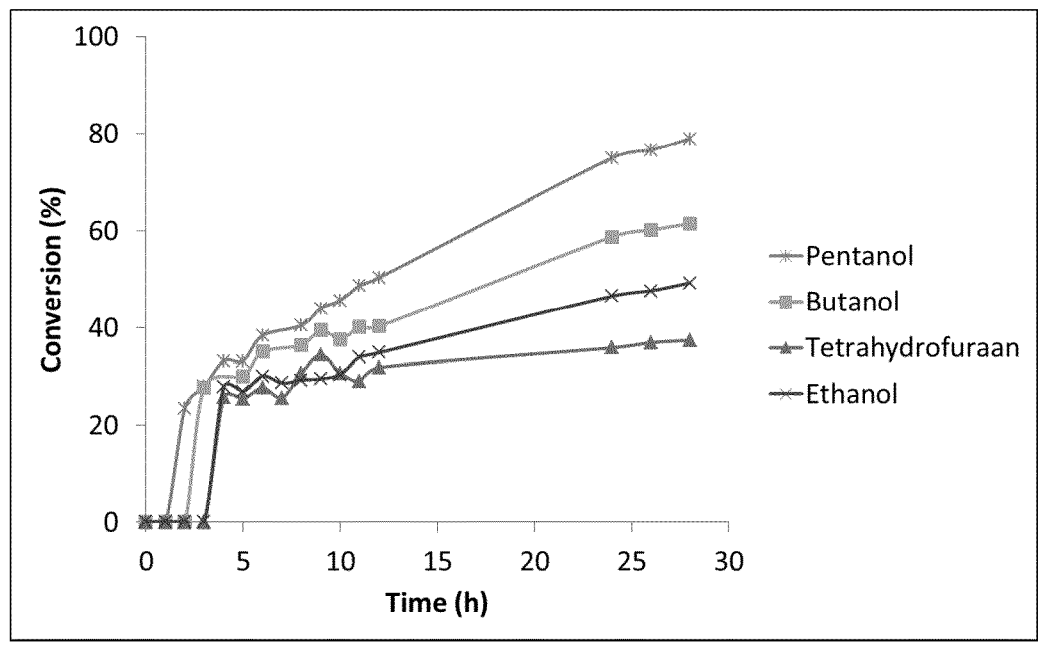
FIG. 3: Example 2—HPLC results of the enzymatic conversion of MEL-A to MEL-C in solvents with different polarities—short term follow-up.
Figure 4:
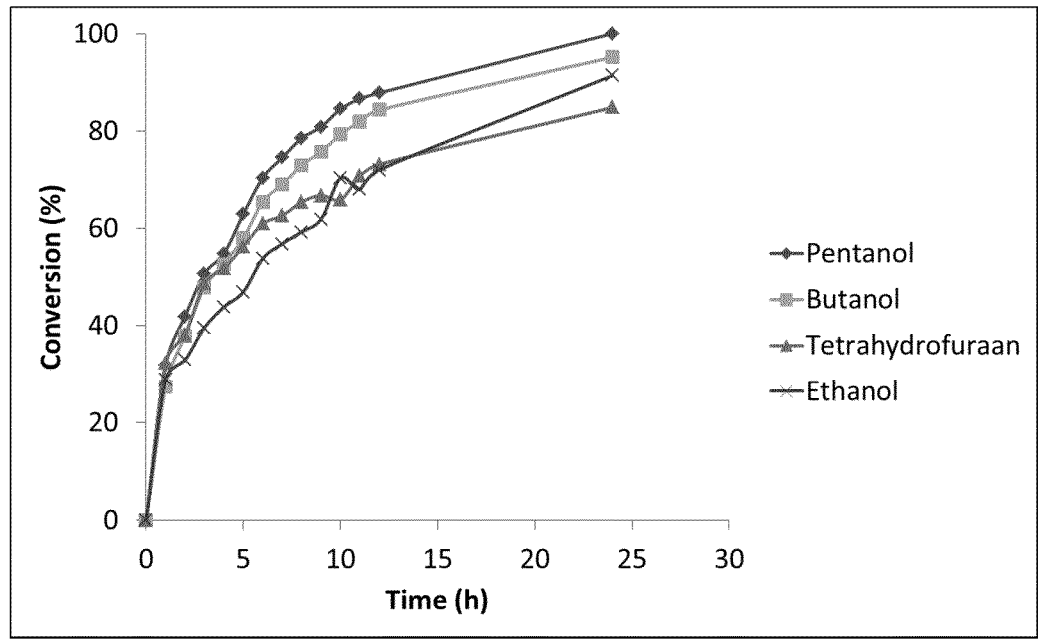
FIG. 4: Example 2—HPLC results of the enzymatic conversion of MEL-B to MEL-D in solvents with different polarities—short term follow-up.
Figure 5:
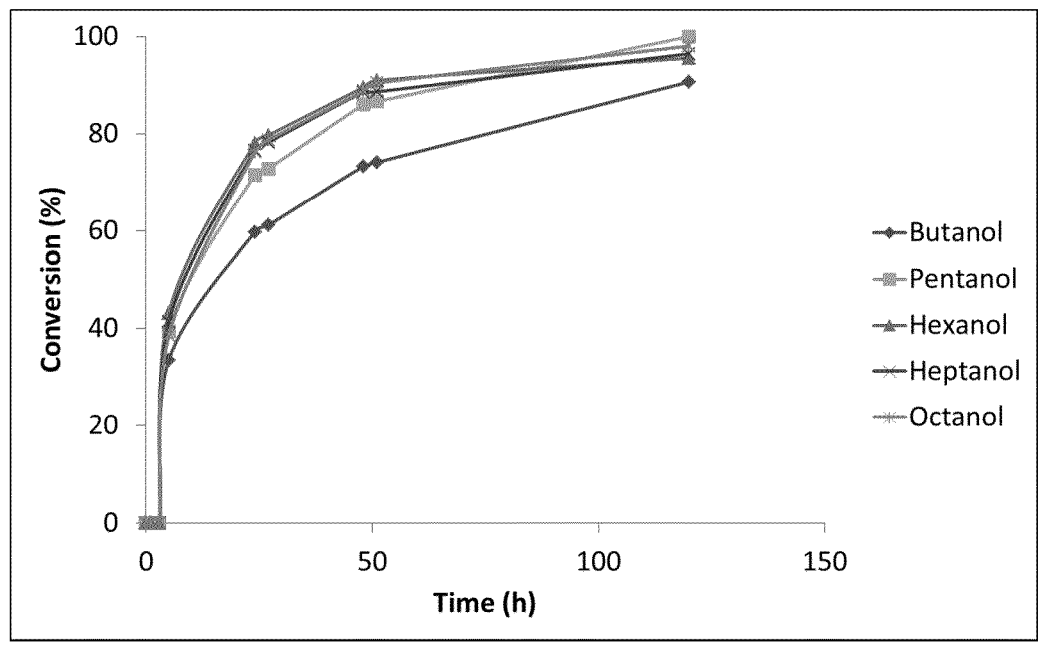
FIG. 5: Example 2—HPLC results of the enzymatic conversion of MEL-A to MEL-C in alcohols with different carbon chain length—long term follow-up.
Figure 6:
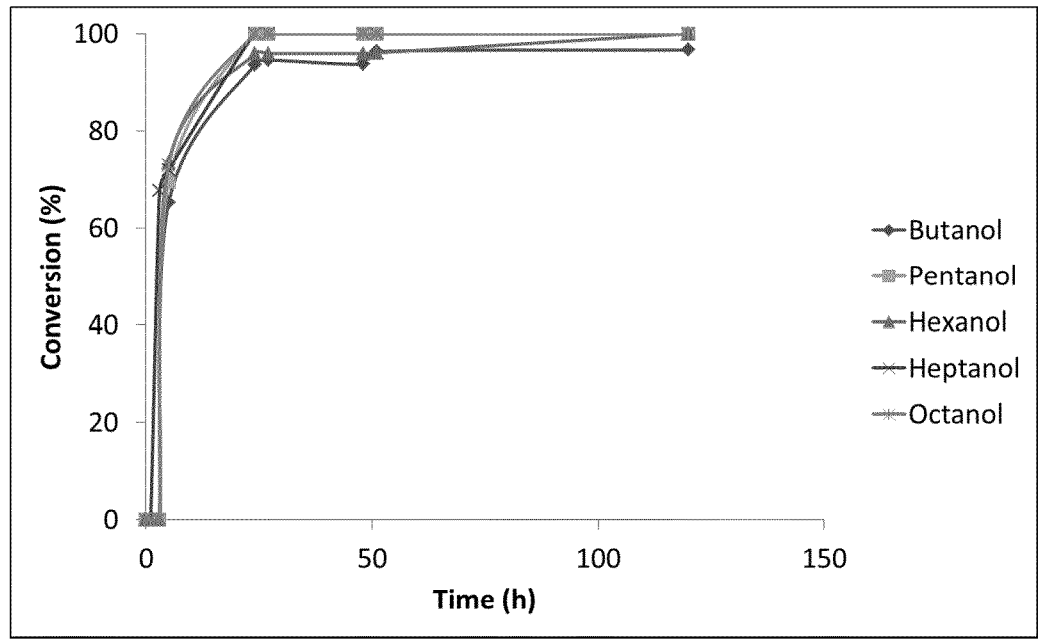
FIG. 6: Example 2—HPLC results of the enzymatic conversion of MEL-B to MEL-D in alcohols with different carbon chain length—long term follow-up.

In the pure solvent, i.e. without the addition of water, after 24 h the conversion of MEL-A to MEL-C was 76% with octanol, 77% with heptanol, 78% with hexanol, 72% with pentanol, 60 with butanol, 47% with ethanol and 36% with THF (FIG. 3). After 5 days (120 h) 95-100 conversion of MEL-A to MEL-C was achieved with pentanol, hexanol, heptanol and octanol (FIG. 5). After 24 h the conversion of MEL-B to MEL-D was complete (>99%) for n-alcohols with a carbon chain length of 5 to 8, namely pentanol, heptanol and octanol. In butanol the conversion reached 95%, in ethanol 91% and in THF 85% (FIG. 4 and FIG. 6).

For both reactions, n-alcohols with a carbon chain length of C5 to C8 proved to be the most suitable.

The difference in kinetics between the deacetylation on C6' on MEL-A and MEL-B could be explained by the difference in solubility of both substrates in the reaction medium or by steric hindrance on the MEL-A molecule due to the acetylation on C4'.

Example 3: Deacetylation of the Fermentation Product Consisting of a Mixture of MEL-A, -B, -C and -D in Butanol Materials and Methods A first TLC sample was prepared by dissolving 0.25 g of the MEL-mix containing MEL-A, -B, -C and D in 10 ml of ethyl acetate. 5 g of the MEL-mix was dissolved in 100 ml of butanol in a 200 ml erlenmeyer flask with screw cap. 5 g of Novozym® 435 were added. The whole was shaken at 180 movements per minute in an incubator at 60° C.

After 2 days and 5 hours (53 hours), the reaction was stopped. The solution was filtered through a paper filter on a funnel.

The filtrate was then filtered through a PTFE filter (0.2 µm) and the collected volume was placed in a vacuum centrifuge at maximum speed (1500 rpm) and 57° C. for 21 hours. A second TLC sample was then prepared by dissolving 0.25 g of the remaining sticky brown syrup into 10 ml of ethyl acetate.

Results:

After 53 hours, the substrate has been almost completely converted into MEL-C and -D (TLC data not shown). Results from example 1 where MEL-A is completely converted into MEL-C in 5 days, suggest that complete conversion of the MEL-mix into MEL-C and MEL-D could be achieved using a slightly longer reaction time and pentanol instead of butanol as the reaction medium.

Example 4: Deacetylation of the Fermentation Product Consisting of a Mixture of MEL-A, -B, -C and -D in the Commodity Alcohol 2-Ethylhexanol Materials and Methods 5 ml of a 14 g/l MEL reference containing MEL-A, -B, -C and -D was dissolved in 2-ethylhexanol. The preparation of this MEL reference was described in the detailed description of the invention. The deacetylation reaction was initiated by adding 50 g/l of Novozym® 435 and incubating at 60° C. and shaken at 270 rpm in closed glass GC headspace vials. Periodically samples were withdrawn for TLC and HPLC analyses. HLPC and TLC analyses were conducted according to Example 1.

Results

Figure 7:
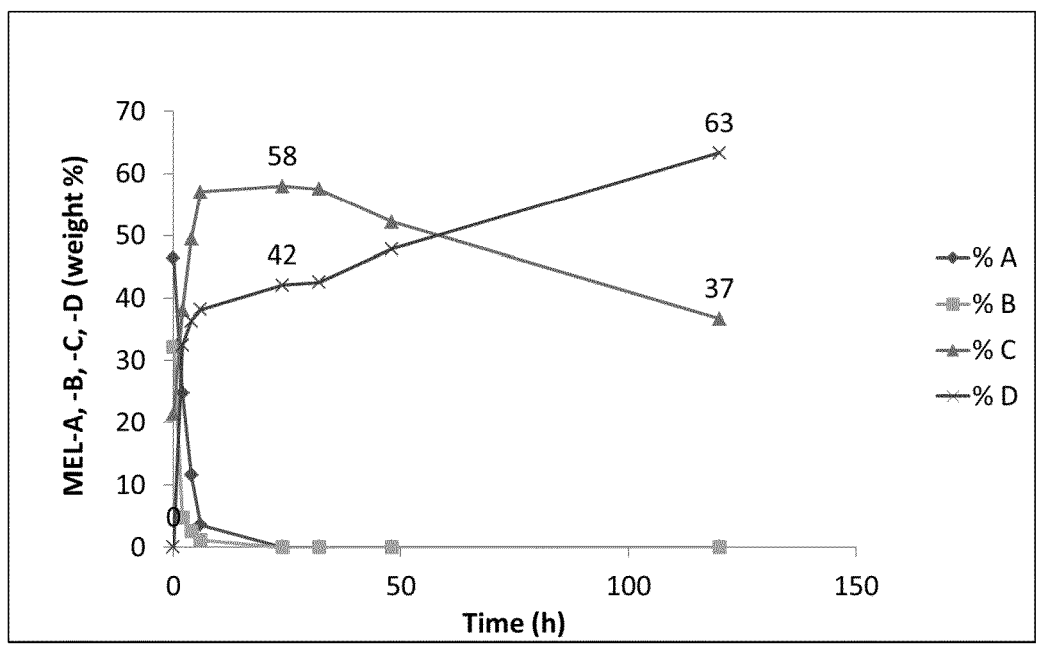
FIG. 7: Example 4—HPLC results of the enzymatic deacetylation of MEL-A, -B, -C, -D mix in 2-ethyl hexanol.

In less than 24 h MEL-A and MEL-B could be completely converted into MEL-C and -D. After 24 h the product contained 58% MEL-C and 42% MEL-D. As the reaction proceeded, MEL-C was gradually converted into MEL-D to end with a product containing 37% MEL-C and 63 MEL-D after 120 h (5 days). The HPLC results are shown in FIG. 7.

Example 5: Deacetylation of MEL-A and -B in Different Commodity Alcohols, Using Novozym® 435

Materials and Methods

Different branched commodity alcohols were used for the deacetylation of MEL-A and MEL-B: isopropanol (C3), isobutanol (C4), tertiary butanol (C4) and 2-pentanol (C5). Pentanol and propanol were also used in this experiment to compare the non-branched with the branched alcohols. 14 g/l of MEL-A and MEL-B were respectively dissolved in 1 ml of each solvent. 0.014 g of MEL was weighed in a 2 ml centrifuge tube with screw cap and 1 ml of solvent was added and the whole was vortexed. A first sample was taken (t=0 h) after which 50 g/l of Novozym® 435 was added to initiate the reactions. The reactions were started by putting the centrifuge tubes in a heating block at 60° C. and 1000 rpm. For TLC and HPLC analyses 51 µL of sample was taken just before the addition of enzyme and after 25 h. TLC and HPLC methods are described in Example 1.

Results

Figure 8:
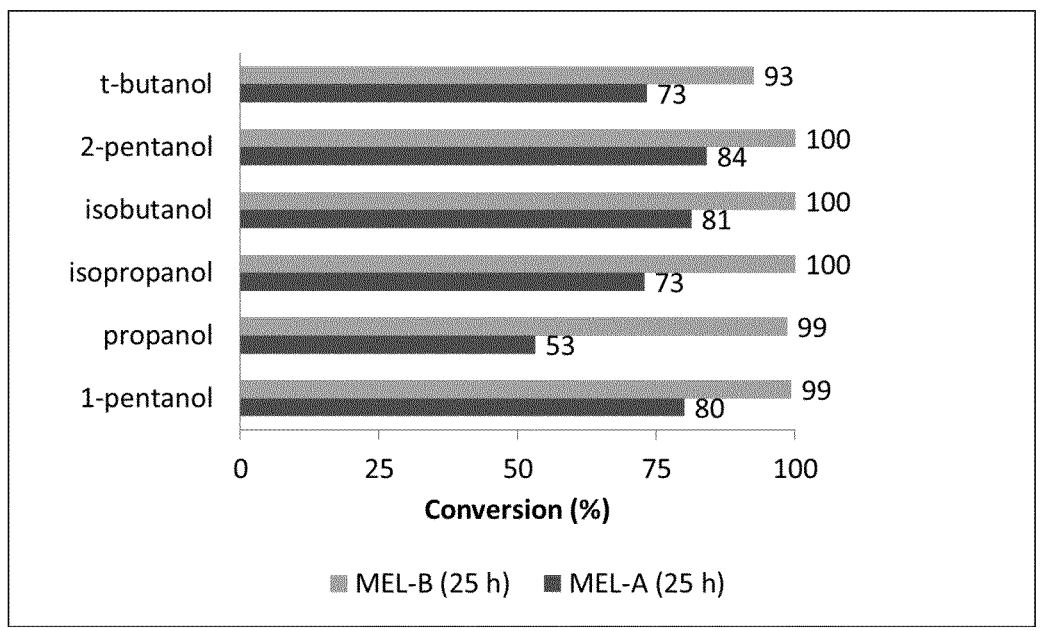
FIG. 8: Example 5—HPLC results of the enzymatic deacetylation of MEL-A and MEL-B in different commodity alcohols (conversion after 25 h).

HPLC results showed that the conversion of MEL-B was much faster than that of MEL-A, as noticed already in Example 2. After 25 h, all the solvents showed a complete conversion of MEL-B. For MEL-A, the highest conversions were achieved in 2-pentanol (84%), isobutanol (81%) and pentanol (80%) (FIG. 8).

Example 6: Deacetylation of MEL-A in the Commodity Alcohols, 2-Ethylhexanol and Isoamyl Alcohol, Using Novozym® 435

Materials and Methods

The deacetylation of MEL-A was carried out in 2 commodity alcohols, 2-ethylhexanol (C8) and isoamyl alcohol (C5). The reaction in pentanol was run in parallel as a reference.

A 14 g/l MEL-A solution was made with 5 ml of each alcohol in glass reaction vials. To each vial 0.25 g of Novozym® 435 was added to initiate the reactions. The vials were incubated at 60° C. and shaken at 240 rpm. During the reactions samples of 100 µl were taken from which 1 µL was used for TLC analysis. From the remaining amount, the solvent was evaporated in a vacuum centrifuge at 60° C. and 9 mbar. The sample was then redissolved in 1 ml of chloroform (the same solvent as used for HPLC analysis) and 50 times diluted.

Results

TLC results showed that the conversion of MEL-A to MEL-C was slower in isoamyl alcohol as compared to 2-ethylhexanol. In 2-ethylhexanol, MEL-A was almost completely converted into MEL-C after 24 h. After 96 h both reaction mixtures presented significant amounts of MEL-D. In isoamyl alcohol almost all MEL-A was converted into MEL-D (TLC data not shown).

Figure 9:
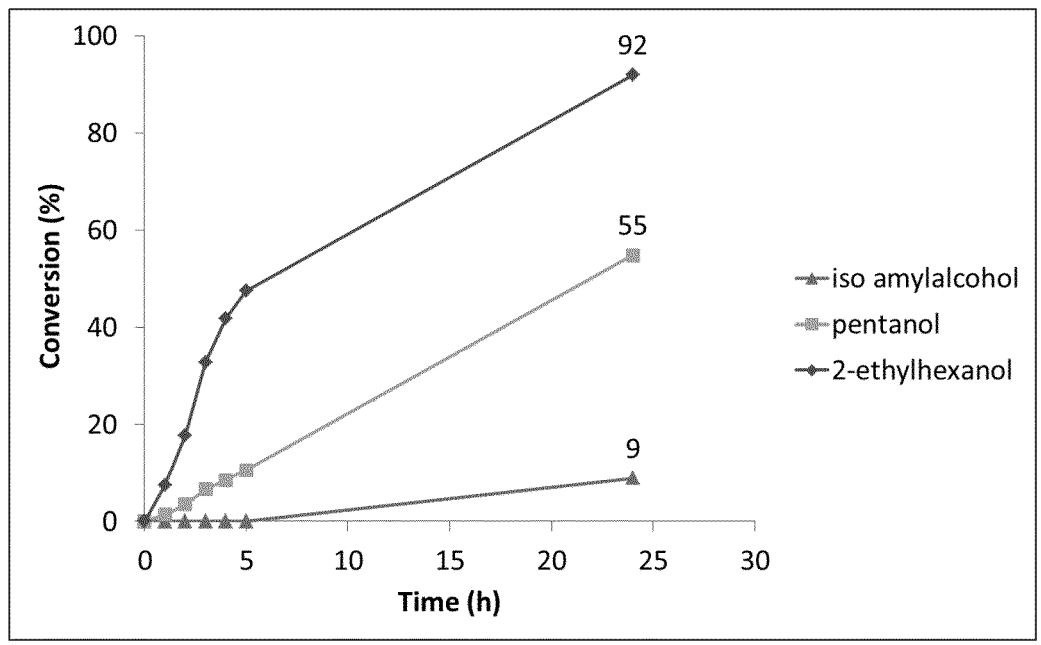
FIG. 9: Example 6—HPLC results of the enzymatic conversion of MEL-A to MEL-C in the commodity alcohols, 2-ethylhexanol and isoamyl alcohol compared to 1-pentanol.
Figure 10:
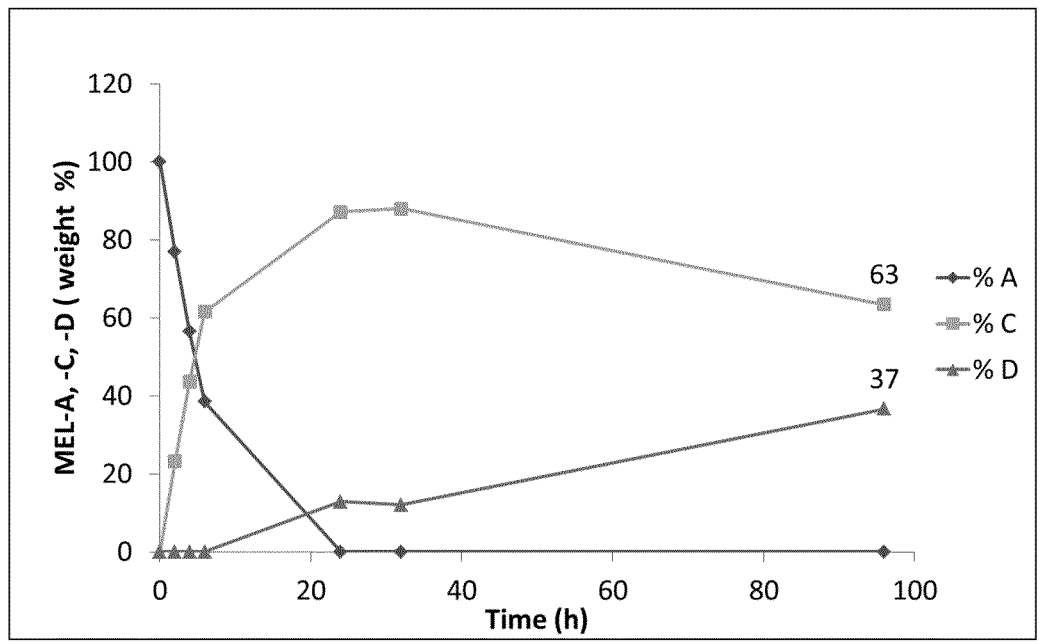
FIG. 10: Example 6—HPLC results of the enzymatic conversion of MEL-A to MEL-C and MEL-D in isoamyl alcohol.
Figure 11:
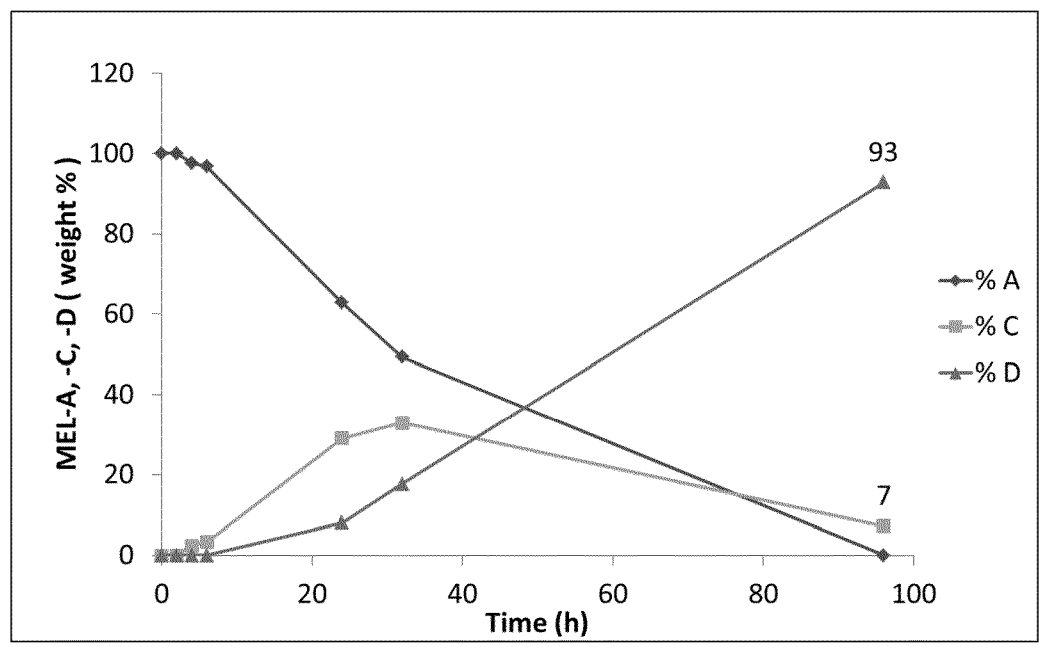
FIG. 11: Example 6—HPLC results of the enzymatic conversion of MEL-A to MEL-C and MEL-D in isoamyl alcohol.

The TLC results were confirmed by HPLC analysis. FIG. 9 shows a comparison of the conversion of MEL-A in the 3 solvents. The conversion is much faster in 2-ethylhexanol (92 after 24 h) compared to 1-pentanol (55%) and isoamyl alcohol (9%). However, Novozym® 435 expresses a different selectivity in 2-ethylhexanol and isoamyl alcohol. The deacetylation of MEL-A in 2-ethylhexanol occurred in 2 steps; first the $R_1$ acetate on the mannose moiety was cleaved to produce MEL-C with a 87% MEL-C yield after 24 h. Subsequently the $R_2$ carbon was deacetylated and yielded 37% MEL-D after 96 h (FIG. 10). In isoamyl alcohol the initial MEL-C formation rate was much lower, but the formation of MEL-D already took place when only 29% of MEL-C was formed resulting in a much higher MEL-D yield of 93% after 96 h. (FIG. 10 and FIG. 11)

Example 7: Effect of Water—Deacetylation of MEL-B in Pentanol with Different Water Concentrations, Using Novozym® 435

Materials and Methods 5 reactions in pentanol were carried out with different water concentrations (0%, 1%, 3%, 5% and 10% (v/v). 14 g/l of MEL-B and 50 g/l of Novozym® 435 were used to carry out the reactions. 0 to 10% of water was added to the MEL-B solution in pentanol. For the 0% water in pentanol, molecular sieve (12% w/v) was added to dry the solvent. The reaction vials were incubated at 60° C. during 24 h. The first 5 hours, every hour a sample of 100 µl was taken. These samples were used for TLC and HPLC analysis.

Before the addition of Novozym® 435, a sample was taken and analyzed using TLC (data not shown). The results showed that the start product contained MEL-B only.

Results

Figure 12:
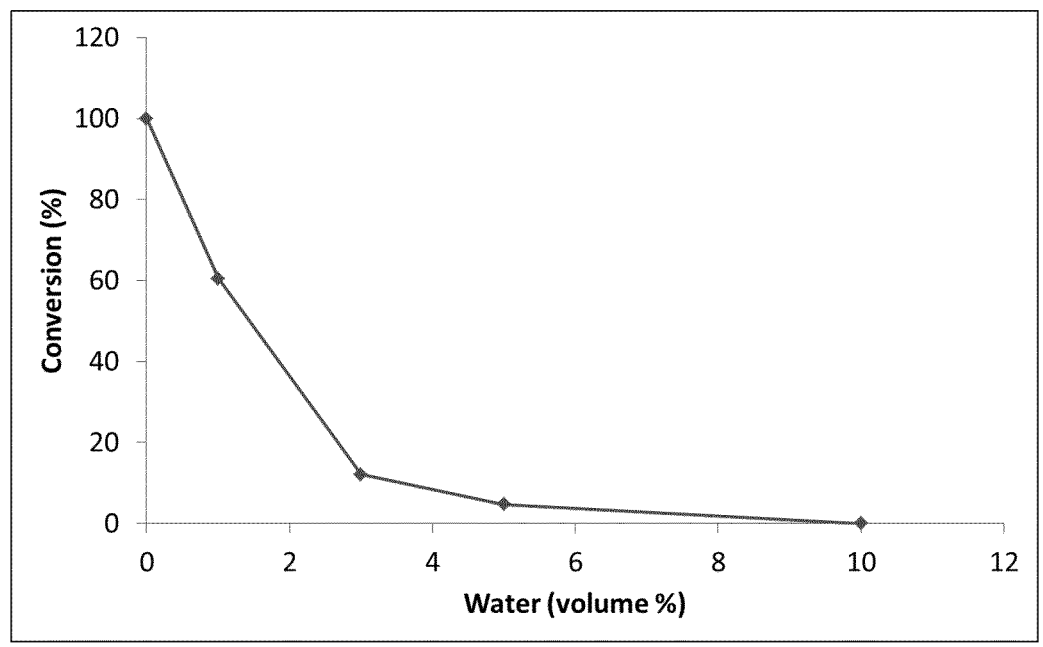
FIG. 12: Example 7—HPLC results of the water concentration profile of the enzymatic deacetylation of MEL-B in pentanol (conversion after 24 hours).

After a reaction time of 24 h a clear trend was visible: the lower the water concentration, the higher the conversion of MEL-B. Based on the quantitative HPLC results, the water concentration profile could be determined for the deacetylation of MEL-B in pentanol (FIG. 12). Here as well it was clear that a lower water concentration promoted a higher the conversion. At a water concentration of 10%, the conversion was even reduced to 0%.

Example 8: Effect of Water—Deacetylation of MEL-A Under Different $a_w$ Values, Using Novozym® 435

Introduction

The activity of an enzyme is correlated to the water that is bound to it. It is difficult to measure and control the amount of water bound to the enzyme. Control of water activity ($a_w$) comes in handy as a way to control bound water and achieve reproducible results, especially in organic solvents that are water immiscible. An $a_w$ value of 0 corresponds to a dry system and a value of 1 to a water-saturated system. At equilibrium the $a_w$ is equal in all phases.

Materials and Methods

A 14 g/l stock solution of MEL-A in 2-ethylhexanol was prepared by dissolving 0.7 g of MEL-A in a 50 ml flask. From this stock solution 5 ml was brought into six 10 ml GC headspace vials. Six times 0.25 g of Novozym® 435 were weighed as well.

Next, the stock solutions and the enzymes were put in jars with saturated salt solutions to pre-equilibrate at the corresponding water activity levels during 18 h at room temperature (Table 1).

TABLE 1

| Vial | Solvent | Salt | $a_w$ |
|---|---|---|---|
| 1 | 2-ethylhexanol | LiBr | 0.064 |
| 2 | 2-ethylhexanol | LiCl | 0.113 |
| 3 | 2-ethylhexanol | $MgCl_2$ | 0.328 |
| 4 | 2-ethylhexanol | $Mg(NO_3)_2$ | 0.529 |
| 5 | 2-ethylhexanol | NaCl | 0.753 |
| 6 | 2-ethylhexanol | $K_2SO_4$ | 0.973 |
| 7 | 2-ethylhexanol | — | 0 |

Before the start of the reaction, a seventh reaction vial was filled with 5 ml of MEL-A stock solution and molecular sieve to reach an $a_w$ of 0. The reactions were initiated by adding the enzymes to the vials with the MEL-A stock solutions and by incubating them at 60° C. and shaking them at 240 rpm. Samples were analysed by HPLC.

Results

Figure 13:
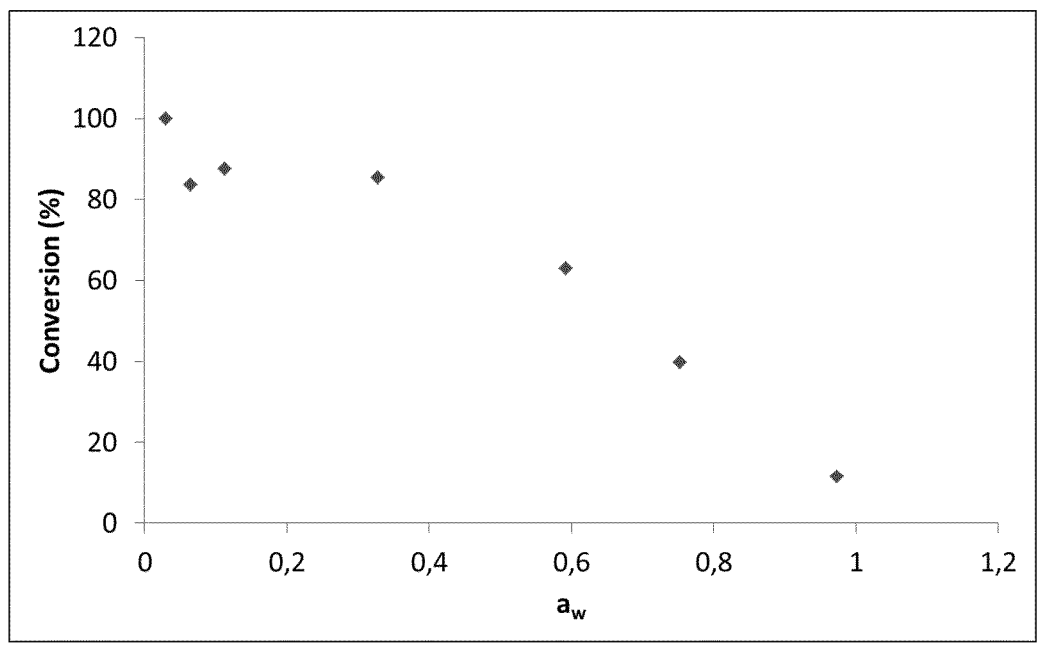
FIG. 13: Example 8—HPLC results of the water activity profile of the enzymatic deacetylation of MEL-A to MEL-C in 2-ethylhexanol (conversion after 24 hours).

FIG. 13 shows the conversion of MEL-A as a function of the water activity. A clear trend is noticeable revealing that at higher $a_w$ values the conversion decreases. 2 points at very low $a_w$ values deviate due to sample taking. At such low moisture levels the $a_w$ can be greatly influenced. At the lowest $a_w$ this did not pose a problem because the molecular sieve controlling the $a_w$ was present in the reaction mix during the entire time. From these results it could be concluded that the optimal $a_w$ for the deacetylation of MEL-A in 2-ethylhexanol using Novozym® 435 is 0. Results from Example 6 already revealed a similar trend based on water percentage added to the reaction mix.

Example 9: Effect of Water—Deacetylation of MEL-B in MeOH, EtOH, PrOH and PeOH—with 10% Water and without Water, Using Novozym® 435

This experiment was set up to verify if the negative effect of water on the deacetylation of MELs in lower alcohols (C1-C3) is as pronounced as in higher alcohols (C5 for example).

Materials and Methods

A series of solutions of 14 g/l MEL-B were prepared in 5 ml of each solvent in glass reaction vials. A second series was prepared in the same way whereafter 10% (v/v) of water was added to the reaction vials. Afterwards from each vial a sample was taken and Novozym® 435 (50 g/l) was added. The reaction vials were incubated at 65° C. and shaken continuously at 240 rpm. Another sample was taken after 22 h when the reaction was ended.

Results

Figure 14:
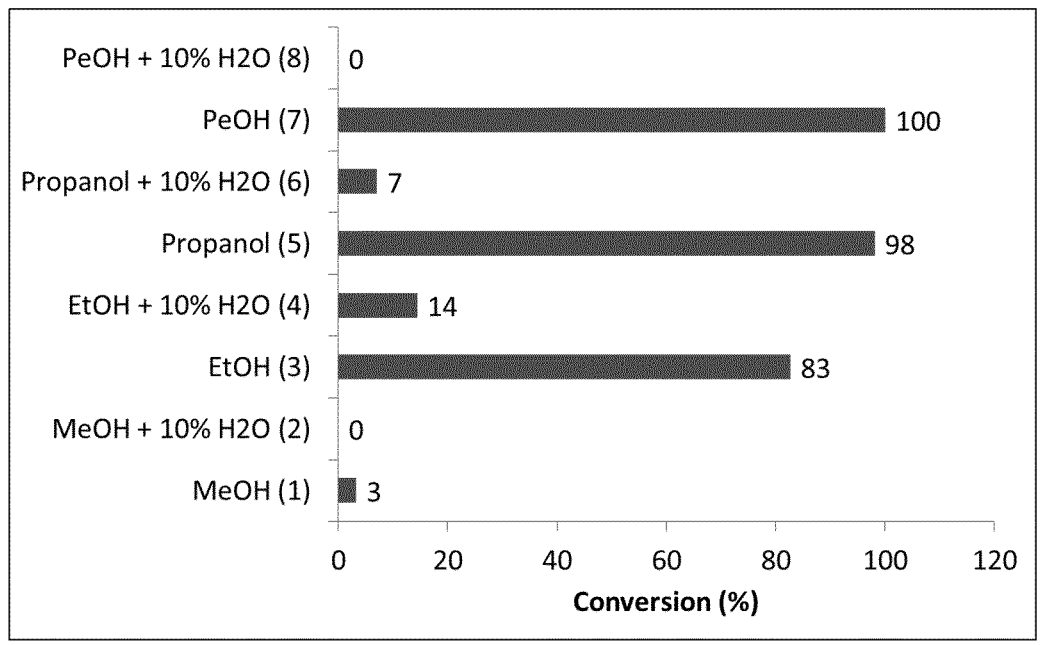
FIG. 14: Example 9—HPLC results of the effect of the alcohol chain length on the deacetylation of MEL-B in the presence of 10% water or without water.

HPLC results showed that in the pure alcohols the conversion increased in function of the alcohol chain length, with a 100% conversion in pentanol, whereas in combination with 10% water the conversion decreased down to 0% in function of the alcohol chain length (FIG. 14). Generally, the conversions were significantly higher without the addition of water.

Example 10: Screening of Different Enzymes for the Deacetylation of MELs

Materials and Methods

As an example for the deacetylation of MELs, MEL-B was used to screen a variety of enzymes. A 14 g/l solution of MEL-B in 1-pentanol was prepared and divided over 22 glass vials. To each vial 50 g/l (or more for enzymes with a low specific activity) of 22 different enzymes were added to initiate the reaction (Table 2). The reaction was carried out at 60° C. and 270 rpm. From each vial a sample was taken before the start of the reaction and one after 23 hours. 1 µl of each sample was spotted on a TLC plate for analysis. The MEL reference containing MEL-A, -B, -C and -D was also spotted for identification. TLC was carried out according to EXAMPLE 1.

Results

Under the used reaction conditions, 7 from the 22 screened enzymes were able to reach (almost) complete conversion of MEL-B to MEL-D in only 23 hours (+++). Esterzyme B2 gave a significant conversion as well(++). Lipozyme® TL IM and RM IM, Transzyme A2 and Esterzyme B1 generated a slight conversion (+). For the other enzymes, no conversion could be detected (-).

TABLE 2

| Enzyme | Company | Deacetylation |
| --- | --- | --- |
| Lipase from *Aspergillus oryzae* | Sigma-Aldrich Co. | - |
| Protease from *Streptomyces griseus* | Sigma-Aldrich Co. | - |
| Protease from *Aspergillus saitoi* | Sigma-Aldrich Co. | - |
| *Candida antarctica* lipase B (Novozym ® 435) | Sigma-Aldrich Co. | +++ |
| Lipase from *Candida rugosa* (Lipomod ™ 34P) | Biocatalysts Ltd. | - |
| Lipase from *Rhizomucor miehei*, immobilized (Lipozyme ® RM IM) | Novozymes A/S | + |
| Lipase from *Thermomyces lanugenosus*, immobilized (Lipozyme ® TL IM) | Novozymes A/S | + |
| Lipase from *Rhizopus oryzae*, powder (Lipase DF Amano 15-K) | Amano Enzyme Inc. | - |
| Lipase from *Penicillium camembertii*, powder(Lipase G Amano 50) | Amano Enzyme Inc. | - |
| *Candida antarctica* lipase A, powder (CalA lyo, FG) | c-LEcta GmbH | - |
| Esterase from *Penicillium roqueforti*, powder (Lipomod ™ 338 MDP) | Biocatalysts Ltd. | - |
| *Candida antarctica* lipase A, aqueous suspension (Novocor ® ADL) | Novozymes A/S | - |
| Transzyme A1 | Transbiodiesel Ltd. | - |
| Transzyme A2 | Transbiodiesel Ltd. | + |
| Esterzyme B1 | Transbiodiesel Ltd. | + |
| Esterzyme B2 | Transbiodiesel Ltd. | ++ |
| CALB immo 8806 | Purolite Ltd. | +++ |
| CALB immo 5587 | Purolite Ltd. | +++ |
| CALB immo PLUS | Purolite Ltd. | +++ |
| CALB immo 5872 | Purolite Ltd. | +++ |
| CALB immo 1090 | Purolite Ltd. | +++ |
| CALB immo 8285 | Purolite Ltd. | +++ |

REFERENCES

Fukuoka, T., Yanagihara, T., Imura, T., Morita, T., Sakai, H., Abe, M., & Kitamoto, D. (2011). Enzymatic synthesis of a novel glycolipid biosurfactant, mannosylerythritol lipid-D and its aqueous phase behavior. *Carbohydrate Research*, 346(2), 266-271. Retrieved from http://www-.sciencedirect.com/science/article/pii/S0008621510005094

José, C., Bonetto, R. D., Gambaro, L. a., Torres, M. D. P. G., Foresti, M. L., Ferreira, M. L., & Briand, L. E. (2011). Investigation of the causes of deactivation-degradation of the commercial biocatalyst Novozym® 435 in ethanol and ethanol-aqueous media. *Journal of Molecular Catalysis B: Enzymatic*, 71, 95-107. doi:10.1016/j.molcatb.2011.04.004

Reichardt, C. (2003). *Solvents and Solvent Effects in Organic Chemistry* (Third edit.). doi:10.1002/9783527632220

The invention claimed is:

1. A method for the enzymatic deacetylation of a mannosylerythritol lipid represented by formula (Ia), to obtain a mannosylerythritol lipid represented by formula (Id),

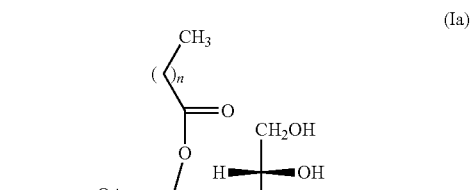

(Ia)

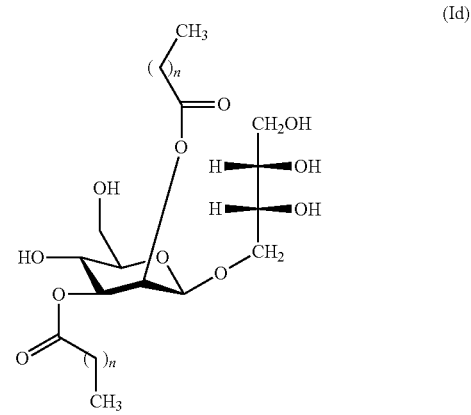

(Id)

the method comprising: incubating a mannosylerythritol lipid represented by formula (Ia), with a lipase in an organic solvent; wherein the organic solvent is selected from the group consisting of C2-C8 alcohols, and combinations thereof; and wherein the organic solvent contains less than 10% water.

2. The method of claim 1, wherein the C2-C8 alcohol is selected from the group consisting of linear and branched C2-C8 alcohols.

3. The method of claim 1, wherein the organic solvent contains less than 9% water.

4. The method of claim 1, wherein the C2-C8 alcohol is selected from the group consisting of ethanol, 1-propanol, 1-butanol, 1-pentanol, 1-hexanol, 1-heptanol, 1-octanol, isopropanol, isobutanol, t-butanol, 2-pentanol, isoamyl alcohol, 2-ethylhexanol, cyclohexanol, and benzylalcohol.

5. The method of claim 1, wherein the organic solvent contains less than 3% water.

6. The method of claim 1, wherein the lipase is a *Candida antarctica* lipase B.

7. A method for the enzymatic deacetylation of a mannosylerythritol lipid represented by formula (Ic), to obtain a mannosylerythritol lipid represented by formula (Id),

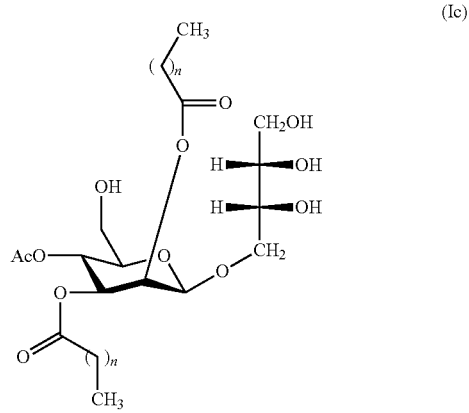

(Ic)

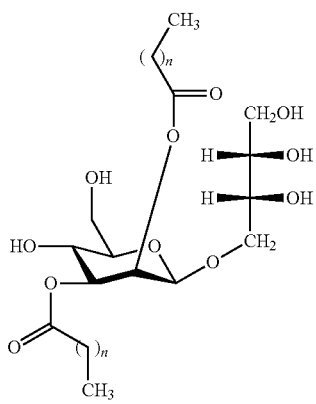

(Id)

the method comprising: incubating a mannosylerythritol lipid represented by formula (Ia), with a lipase in an organic solvent; wherein the organic solvent is selected from the group consisting of C2-C8 alcohols, and combinations thereof; and wherein the organic solvent contains less than 10% water.

8. The method of claim 7, wherein the C2-C8 alcohol is selected from the group consisting of linear and branched C2-C8 alcohols.

9. The method of claim 7, wherein the organic solvent contains less than 9% water.

10. The method of claim 7, wherein the C2-C8 alcohol is selected from the group consisting of ethanol, 1-propanol, 1-butanol, 1-pentanol, 1-hexanol, 1-heptanol, 1-octanol, isopropanol, isobutanol, t-butanol, 2-pentanol, isoamyl alcohol, 2-ethylhexanol, cyclohexanol, and benzylalcohol.

11. The method of claim 7, wherein the organic solvent contains less than 3% water.

12. The method of claim 7, wherein the lipase is a *Candida antarctica* lipase B.

* * * * *

UNITED STATES PATENT AND TRADEMARK OFFICE
CERTIFICATE OF CORRECTION

PATENT NO. : 10,378,036 B2
APPLICATION NO. : 15/552860
DATED : August 13, 2019
INVENTOR(S) : Eliane Yvonne Goossens and Marc Victor Henri Wijnants Page 1 of 1

It is certified that error appears in the above-identified patent and that said Letters Patent is hereby corrected as shown below:

On the Title Page

Column 2, Line 20, item (56), references cited, publications, cite no. 8, delete:
"“Lipase-catalyzed asymmetric acylation in the chemoenzymatic synthesis of furan-based alcohols”, Nara et al., Tetrahedron Asymmetry, Pergamon Press, Ltd., Oxford, GB, vol. 24, Feb. 12, 2013 pp. 142-150."
And insert:
--"Lipase-catalyzed asymmetric acylation in the chemoenzymatic synthesis of furan-based alcohols", Hara et al., Tetrahedron Asymmetry, Pergamon Press, Ltd., Oxford, GB, vol. 24, Feb. 12, 2013 pp. 142-150.--, therefor.

Signed and Sealed this
Fourteenth Day of April, 2020

Andrei Iancu
*Director of the United States Patent and Trademark Office*